United States Patent [19]

Nakao et al.

[11] Patent Number: 5,575,806
[45] Date of Patent: Nov. 19, 1996

[54] BIOPSY FORCEPS WITH TISSUE EJECTION MEANS

[76] Inventors: Naomi Nakao, 303 E. 57th St., New York, N.Y. 10022; John V. Mizzi, 30 Cramer Rd., RFD #3, Poughkeepsie, N.Y. 12603

[21] Appl. No.: 401,818

[22] Filed: Mar. 10, 1995

[51] Int. Cl.$^6$ ............................................. A61B 10/00
[52] U.S. Cl. ................................... 606/207; 128/751
[58] Field of Search ....................... 128/751, 749; 606/205–208

[56] References Cited

U.S. PATENT DOCUMENTS

| | | | |
|---|---|---|---|
| 4,721,116 | 1/1988 | Schintgen et al. | |
| 4,763,668 | 8/1988 | Macek et al. | 128/751 |
| 4,785,825 | 11/1988 | Romaniuk et al. | 128/751 |
| 5,082,000 | 1/1992 | Picha et al. | 128/751 |
| 5,172,700 | 12/1992 | Bencini et al. | 128/751 |
| 5,370,659 | 12/1994 | Sakashita | 606/205 |
| 5,373,854 | 12/1994 | Kolozsi | 128/749 |

FOREIGN PATENT DOCUMENTS

9102493  3/1991  WIPO ................................... 606/206

*Primary Examiner*—Michael Powell Buiz
*Assistant Examiner*—Patrick W. Rasche
*Attorney, Agent, or Firm*—Abelman, Frayne & Schwab

[57] ABSTRACT

An improved biopsy forceps for retrieving a tissue sample from an internal organ is provided with flexible resilient means for ejecting a tissue sample from the cups after the sample is retrieved from the internal organ. The ejector means can comprise a leaf spring extending between the cups and biased in a convex distal direction so that it springs outward when the cups are fully opened, ejecting the tissue sample. An actuating wire has a spring latch for moving the leaf spring to the ejection position and for returning it to a position inside the cups. The wire disengages from the cups so that it can extend distally no eject the sample. A latch mechanism at the proximal end of the wire selectively prevents actuation.

18 Claims, 5 Drawing Sheets

BIOPSY FORCEPS WITH TISSUE EJECTION MEANS

FIELD OF THE INVENTION

The invention relates to flexible biopsy forceps used in conjunction with an endoscope and rigid forceps used with a laproscope for retrieval of a tissue sample from the interior of a patient's body.

BACKGROUND OF THE INVENTION

Flexible biopsy forceps are used in conjunction with a fiberoptic endoscope as follows: the endoscope is inserted into the stomach, colon or other hollow organ of the patient's body, an abnormality is visualized, and the flexible biopsy forceps is introduced through the biopsy channel of the endoscope. The distal end of the biopsy forceps is comprised of two opposed sharp-edged cups that are operably attached by means of pivot arms to a wire passing on the interior of a flexible cable. Actuation means operably connected to the proximal ends of the flexible cable and wire cause the cups to move between an open and closed position.

When the forceps' distal end is properly positioned at the sampling site, the cups are moved to the open position, advanced to contact the tissue and then closed on the tissue, grasping and severing a sample of tissue that is held within the closed cups while the forceps is withdrawn from the patient.

The rigid forceps are employed in conjunction with the laproscopic procedure in a similar manner. With both types of the device, after the forceps has been removed from the endoscope, the tissue sample must then be placed into an appropriate receptacle that contains a preservative (e.g., formalin). In many instances, it is difficult to remove the sample from the forceps cup. Each of the cups of the biopsy forceps is provided with a small opening, or hole, in the central region to receive the end of a needle or other pointed implement. The doctor or assisting personnel will typically use a needle to pry the tissue out of the cup, or otherwise dislodge the sample from the distal end of the forceps. This task is difficult and cumbersome in itself, and dangerous since there are occasions in which medical personnel have been stuck by the needle. If the patient is infected with the HIV virus, or hepatitis, or another contagious disease, the assistant will be infected as well. An additional risk to the medical personnel from an infectious sample is posed by the sharp cutting edges of the cups themselves.

It is therefore an object of the invention to provide a modified biopsy forceps that will eject the biopsy sample from the distal end of the forceps into a convenient receptacle by manipulation of interconnected control means at the proximal end of the forceps.

It is another object of this invention to provide an improved biopsy forceps having means for ejecting the tissue sample that can be incorporated into forceps of current construct with a minimal change in design.

Another object of the invention to provide tissue sample ejecting biopsy forceps that are easy to use and that operate in the same manner to remove tissue samples as the prior art forceps.

A further object of the invention is to provide an improved biopsy forceps from which the tissue sample can be safely ejected without having the medical personnel directly contact or manipulate the distal end of the forceps.

These and other objects are met by the improved biopsy forceps that are described below.

BRIEF DESCRIPTION OF THE INVENTION

As broadly contemplated, the biopsy ejecting forceps of the invention comprises tissue sample ejection means located at the distal end of the forceps that moves in relation to the cups to contact the sample inside of the cups and dislodge it as the cups are moved beyond the open position used during the tissue collection procedure. This is done by control means located at the proximal end of the forceps.

In a preferred embodiment, the tissue sample ejection means is attached to the cups and is positioned in the interior of the cups maintaining a concave configuration while the cups are closed and also while the cups are opened to sever the tissue sample.

In the practice of the invention, the sample ejecting means is remotely activated by control means located at the proximal end of the forceps by the axial movement of at least one wire located in the flexible cable that is secured to the distal and proximal ends of the forceps.

DETAILED DESCRIPTION OF THE INVENTION

Figure 1:
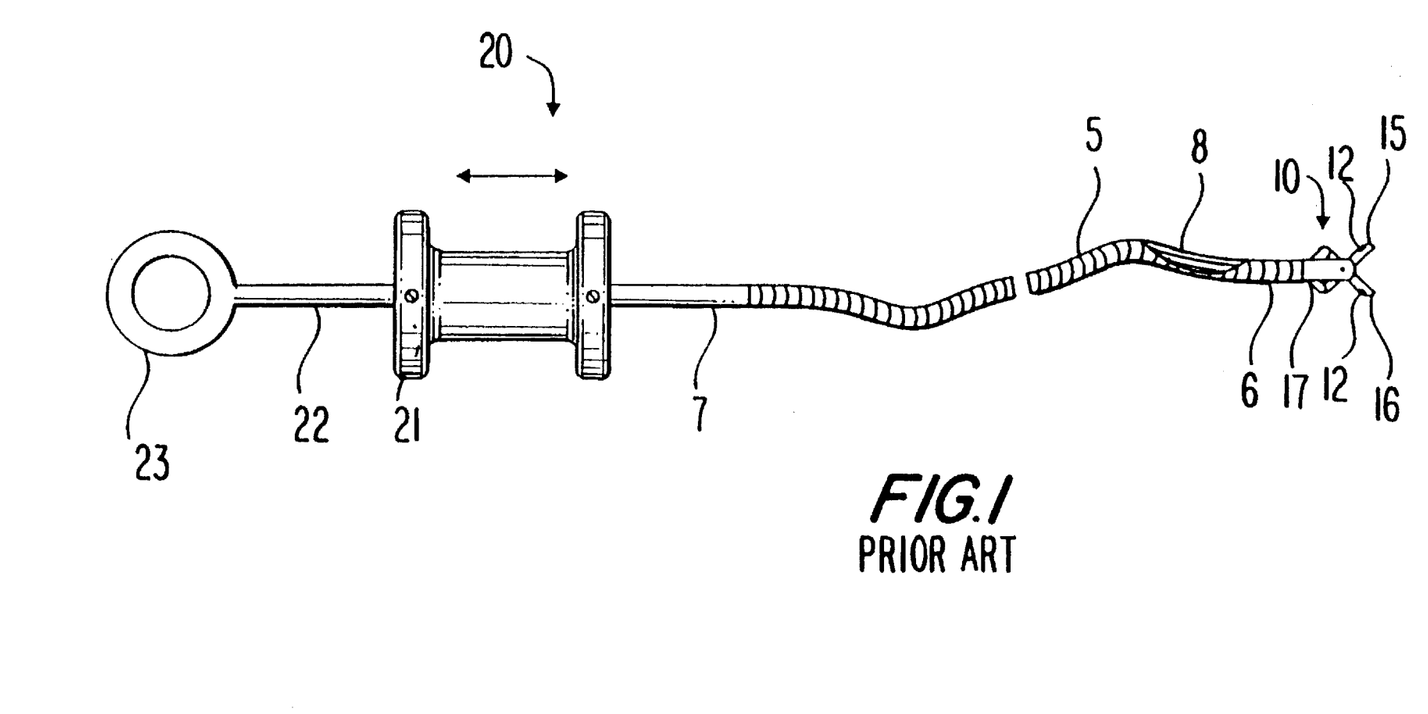
FIG. 1 is a partial cut-away view of a conventional biopsy forceps of the prior art.

A conventional biopsy forceps 1 known in the art is shown in FIG. 1. The forceps comprises a hollow, flexible cable 5 having a distal end 6 and a proximal end 7. An actuating wire 8 is slidably disposed within the cable and extends from the distal to the proximal ends of the cable. At the distal end of the cable is a tissue sample collection means 10, typically comprising two opposing cups 15 and 16 pivotally attached to a clevis 17 depending from the cable 5. The cups are operably attached to the wire 8, so that sliding the wire distally opens the cups, and sliding the wire proximally closes the cups.

At the proximal end 7 of the cable 5 is an actuation means 20, typically comprising a spool 21 slidably mounted on a shaft 22. The shaft has a finger or thumb grip 23 depending from its proximal end. The cable 5 is mounted to the shaft 22. The wire 8 is operably attached to the spool 21, so that an axial sliding movement of the spool 21 on the shaft 22 will produce a similar movement of the wire 8 within the cable 5, thus opening and closing the cups 15 and 16. The opposing edges of the cups are sharpened. When the biopsy forceps is in use, a surgeon opens and closes the cups 15 and 16 by sliding the spool 21 on the shaft 22. The sharpened edges of the cup engage the tissue and sever a small sample which is retained in the cavity formed by the closed cups. Holes 12 are commonly provided in the cups 15 and 16 to permit fluid to drain from the cups.

As explained above, the tissue sample can be difficult to dislodge from its position in or between the cups 15 and 16, and a small implement, such as a needle, must be manually applied by medical personnel to pry the sample from the distal end. Where such holes 12 are provided, medical personnel will insert a small implement through hole 12 to aid in dislodging the sample from the cups.

Figure 2:
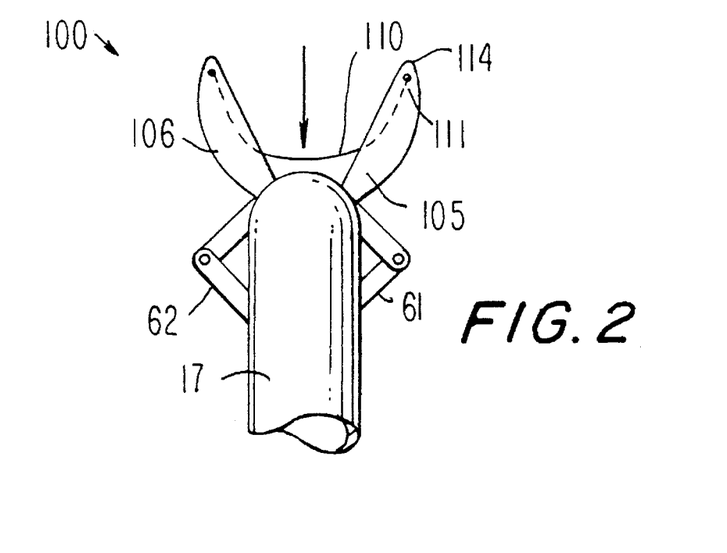
FIG. 2 is a partial view of the distal end of one preferred embodiment of the invention, in a partially opened position.

A preferred embodiment of the biopsy ejection forceps comprising tissue sample collection means 100 is shown in FIG. 2. The cups 105 and 106 are pivotally attached to the clevis 17, and are actuated by the scissor links 61 and 62 as known in the art. An ejection band 110 extends between the cups 105 and 106 at locations 111 and 112 proximate the leading edge 114 of the cups. It is preferred that the ejection band be pivotally attached to the cups at locations 111 and 112, although another attachment, such as a cantilever attachment, can be used while still falling within the scope of the invention. In one embodiment, the ejection band 110 has four tabs 115 (shown in FIG. 4) extending from the four corners of the band in the transverse direction. These tabs engage holes 116 (shown in FIG. 8) provided in the cups 105 and 106 at locations 111 and 112, and permit the band to freely pivot about two transverse axes at locations 111 and 112.

The ejection band 110 can be made from a band of thin, springy stainless steel or other springy material, such as a highly resilient polymer with high tensile strength. In the case of stainless steel, the band can be coated with a release coating, such as Teflon®, to facilitate the removal of the tissue sample from the cups.

Figure 3:
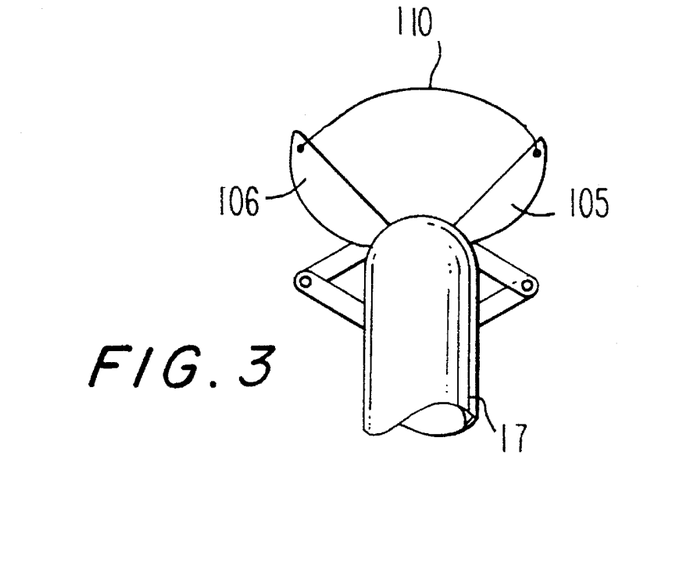
FIG. 3 is a partial view of the distal end of the biopsy ejection forceps of FIG. 2 in a fully opened position.

In its unrestrained state, the ejection band 110 has an arcuate shape with a normally convex face 109 of the band facing the distal direction, away from the cups 105 and 106 as shown in FIG. 3. Before performing a tissue sample retrieval procedure, the band 110 is toggled inward, so that the normally convex surface 109 becomes concave, forming a tissue-receiving hollow 113 within the cups 105 and 106. The ejection band 110 is maintained in this configuration during the surgical procedure by limiting the angle A to less than about 100°. This, in turn, limits the distance between points 111 and 112, and prevents the ejection band from returning to its unrestrained or convex configuration.

After completing the biopsy procedure, the tissue sample (not shown) can be ejected from the tissue collection means 100 by increasing the angle A between the cups 105 and 106 so that it exceeds approximately 100°. The distance between points 111 and 112 is then great enough to permit the ejection band 110 to return to its predisposed arcuate shape, with surface 109 convex in the distal direction, as shown in FIG. 3. The tissue sample, which was contained within the hollow 113 (FIG. 2), is dislodged from the band into a specimen container under the force of the spring-like motion the band. If the specimen sticks to the band, it can be conveniently tapped off or brushed off against the side of the sample container.

The band 110 must be returned to its concave configuration before the forceps can be used again. Any effort to close the cups 105, 106 while the band 110 is in the convex configuration, the band will bow out more and prevent closing of the cups. In the embodiment of the invention illustrated by FIG. 2, band 110 is returned to its concave configuration by completely opening the cups 105 and 106 (where angle A equals approximately 120°), pushing the distal end of the forceps against a flat surface, thereby flattening the band and forcing it between the cups, and then closing the cups while maintaining the distal end of the forceps in contact with the flat surface.

Figure 5:
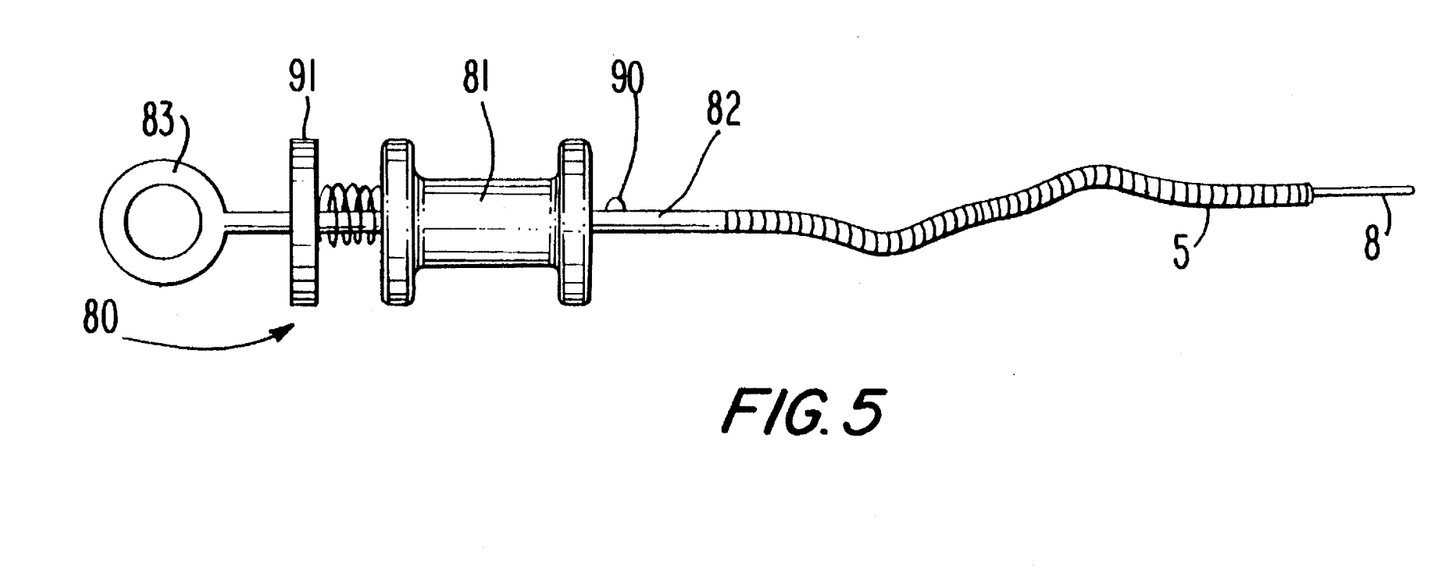
FIG. 5 is a side view of the proximal end of one preferred embodiment of the improved forceps of the invention.
Figure 6:
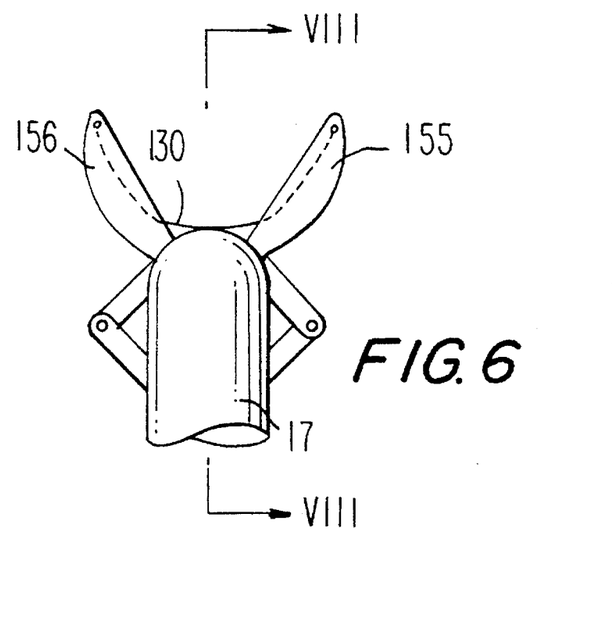
FIG. 6 is a partial view of the distal end of another embodiment of the biopsy ejection forceps of the invention, in a partially opened position.

The preferred actuation means 80 for use with the biopsy ejection forceps of the invention is shown in FIG. 5. A spool 81 is slidably mounted on a shaft 82 with a grip 83 depending from its proximal end. The cable 5 is mounted to the shaft 82. The wire 8 is operably attached at its proximal end to the spool 81, so that a sliding movement of the spool 81 on the shaft 82 will produce a similar movement of the wire 8 within the cable 5, thus opening and closing the cups by linkage means attached to the distal end of wire 8.

The travel of the spool 81 along the shaft 82 in the distal direction is limited by the latch 90. In this preferred embodiment, the position on the shaft 82 at which the spool 81 abuts the latch 90 corresponds to the position of the tissue sample collection means wherein the cups 105, 106 are opened to an angle of approximately 90°. This cup position is used by the surgeon during the operative procedure to place the cups over the tissue sample to be removed. The surgeon then slides the spool 81 in the proximal direction, away from the latch 90, to close the cups.

An ejection actuator plate 91 is slidably mounted on the shaft 82 on the proximate side of spool 81. The ejection actuator plate 91 is operably attached to the latch 90 such that a distal movement of the actuator plate 91 releases the latch 90. When the tissue sample is to be ejected from the cups 105 and 106, the ejection actuator plate is moved in the distal direction, first releasing the latch 90, and then contacting and moving the spool 81 until the tissue sample collection means reaches the position wherein the cups are opened to an angle of approximately 120°, the ejection band flips from a concave to a convex configuration, and the tissue sample is ejected from the forceps.

Figure 4:
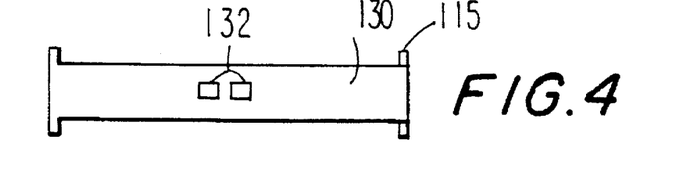
FIG. 4 is a plan view of an ejection band of the forceps of FIG. 2.
Figure 7:
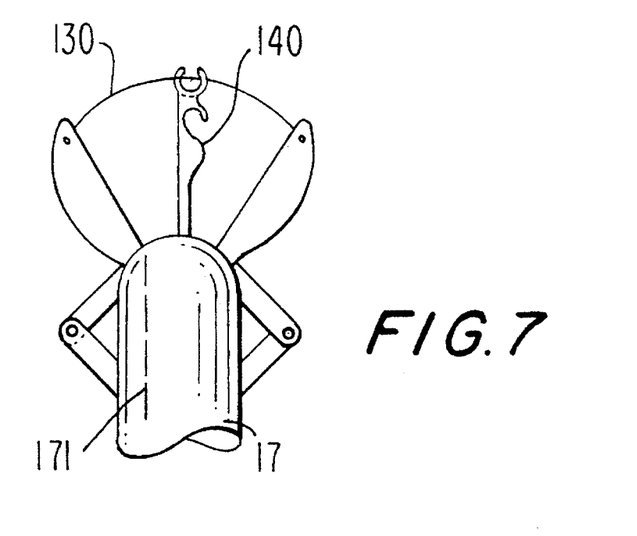
FIG. 7 is a partial view of the forceps of FIG. 5 in a fully opened position.
Figure 9:
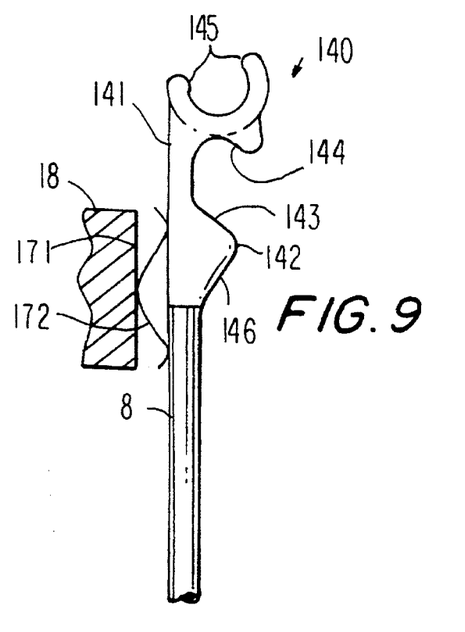
FIG. 9 is a plan view of an actuator and partial sectional view of the forceps of FIG. 5.

A further embodiment of the forceps comprises the tissue sample collection means 100, shown in FIGS. 4, 7 and 9. The cups 155 and 156 are pivotally attached to the clevis 17, and an ejection band 130 extends between the cups, as previously described. This embodiment is further provided with an actuator 140, which is integral with the distal end of wire 8, as shown in FIG. 9. The actuator 140 provides for the return of the ejector band 130 to the concave position by manipulation of the wire 5 from the proximal end of the forceps. The actuator 140 can be formed from the flattened end of wire 8 using an appropriate process such as die punching or laser cutting.

Figure 8:
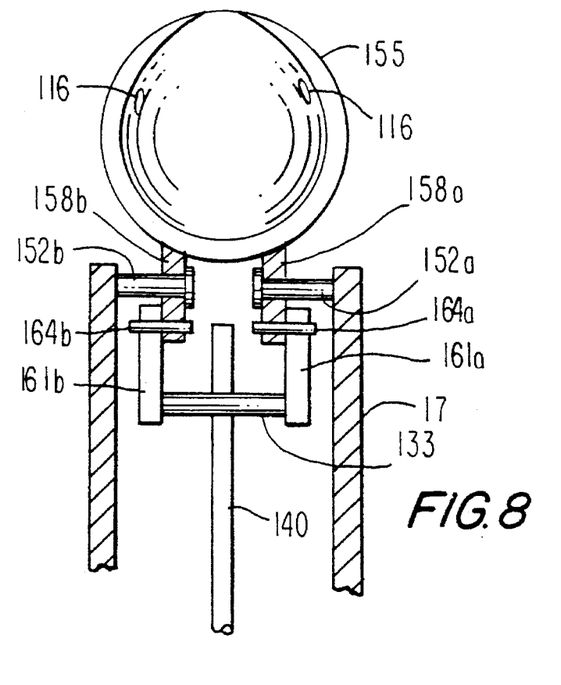
FIG. 8 is a sectional view of an actuator of the forceps of FIG. 5 taken along section line VIII—VIII.

As shown in FIG. 8, the mechanism for opening and closing the cups 155 and 156 is separated into side a and side b to provide room in the center of the mechanism for the actuator 140. While FIG. 11 shows only a mechanism for actuating cup 155, it should be understood that a similar mechanism for cup 156 is also positioned within the clevis 17.

An operating pin 133 is pivotally attached to scissor links 161a, 161b at their proximal ends and pin 133 extends from side a to side b. The operating pin 133 is engaged by the actuator 140 as described below.

Cup 155 has integral levers 158a and 158b depending from its proximal edge. Levers 158a and 158b are pivotally attached near their centers to the clevis 17 by opposing pins 152a, 152b, which protrude from opposite inside walls of the clevis, leaving a space between them for passage of actuator 140. The pins 152a, 152b also support the integral levers 159a and 159b (not shown) associated with cup 156.

The proximal ends of the levers 158a and 158b are pivotally attached to the distal ends of the scissor links 161a and 161b, respectively, by pins 164a and 164b, respectively. The cups 155 and 156 can thereby be opened and closed by moving operating pin 133 in the distal and proximal directions, respectively.

As shown in FIG. 9, the actuator 140 has a flat, longitudinal edge 141. A leaf spring 172 or similar biasing means is disposed within the clevis 17 to urge actuator 140 away from a surface 171 (see FIG. 7) provided in the clevis 17 for this purpose. The actuator 140 is thereby biased against the operating pin 133 for enhanced engagement.

Opposite edge 141, the actuator 140 has a hook 144 for engaging the operating pin 133 when the wire 8 moves the actuator 140 in the proximal direction, closing the cups 155 and 156. The actuator 140 further has a lateral protrusion 142 at its proximal end. As the wire 5 moves in the distal direction, a surface 143 on the protrusion 142 is urged by the wire and by the leaf spring 172 into engagement with the operating pin 133, pushing the pin distally and opening the cups 155 and 156.

In order to remove tissue from the cups, ejection actuator plate 91 is moved distally (FIG. 5), permitting the spool 81 to move past the latch 90. The wire 8 moves the actuator 140 distally, forcibly engaging the protrusion 142 with the operating pin 133, and completely opening the cups 155 and 156. A camming force between the surface 143 and the pin 133 overcomes the biasing force of leaf spring 172, permitting the protrusion 142 to travel past the operating pin 133.

A spring latch 145 of the actuator 140 is then permitted to travel between the open cups 155 and 156 and engage the engagement holes 132 in the ejector band 130 (FIG. 4). The actuator continues its excursion between the cups until the ejector band 130 assumes its convex-outward orientation, as shown in FIG. 7. It is not necessary in this embodiment to bias the ejector band convexly, or to overtravel the cups to 120°, since the ejector band is moved under a positive force between its two configurations.

The ejector band 130 is returned for subsequent use to its concave configuration by retracting the actuator 140. Because the spring latch 145 is engaged in the holes 132 in the ejector band 130, the retracting actuator pulls the ejector band into a concave configuration. Further travel of the actuator 140 disengages the spring latch 145 from the holes 132. Surface 146 of the actuator protrusion 142 then engages the operating pin 133, closing the cups 155, 156. Finally, the calming force of the surface 146 against the operating pin 133 deflects the leaf spring 172, permitting the protrusion 142 to pass to the proximal side of the operating pin 133.

It will be understood that spring latch 145 may be a single protrusion engaging a single hole 132 in the ejection band 130; other configurations for operably joining these two elements will be apparent to those skilled in the art.

As will also be apparent to one skilled in the art, those elements which are described as having been formed from the flattened end of the wire, and therefore integral with the wire, can also be fabricated as a separate element and thereafter welded or otherwise secured to the end of the wire.

Other configurations of the ejection biopsy forceps within the scope of the invention, such as additional combinations of the embodiments shown, will be apparent to one skilled in the art.

We claim:

1. A biopsy forceps for retrieving a tissue sample from an organ, comprising:

a flexible, hollow cable with a proximal end and a distal end;

a plurality of opposing cups pivotally attached to said distal end of said hollow cable for severing the tissue sample from the organ;

tissue sample ejection means disposed generally transverse to the axis of the cable in a proximal end of said cups;

a wire slidably disposed within said hollow cable and operably connected to said cups whereby sliding said wire opens and closes said cups;

said wire further being connected to said ejection means whereby sliding said wire moves said means between said cups, ejecting the tissue sample from the cups.

2. The biopsy forceps of claim 1, further comprising a mechanism for opening and closing the cups, wherein said mechanism is comprised of two sides that are spaced apart to provide a passageway for said wire.

3. The biopsy forceps of claim 1, wherein said wire has a flattened area with a hook and a protrusion proximal said hook for releasably engaging an operating pin operably connected to said opposing cups.

4. A biopsy forceps for retrieving a tissue sample from an organ, comprising:

a flexible, hollow cable with a proximal end and a distal end;

a pair of opposing cups pivotally attached to said distal end of said hollow cable for severing the tissue sample from the organ;

a leaf spring extending between said opposing cups, said leaf spring being biased to assume a convex configuration projecting outwardly from the distal ends of the open cups;

said leaf spring being constrained between said cups in a concave configuration at the proximal end of said cups when said cups are closed, whereby when said cups are fully opened, said leaf spring returns to said convex configuration, to thereby eject the tissue sample.

5. The biopsy forceps of claim 4, wherein said leaf spring returns to said convex configuration when said cups are opened more than 100°.

6. The biopsy forceps of claim 4, wherein said leaf spring is pivotally attached to said cups.

7. The biopsy forceps of claim 6, wherein said leaf spring is generally rectilinear and has four tabs extending transversely from the corners of said leaf spring, and each of said cups has two holes for pivotally receiving said tabs.

8. The biopsy forceps of claim 4, further comprising a wire slidably disposed within said cable and operably attached to said cups; and means attached to said proximal end of said cable for positioning the ends of said wire in three positions.

9. A biopsy forceps for retrieving a tissue sample from an organ, comprising:

a flexible, hollow cable with a proximal end and a distal end;

a pair of opposing cups pivotally attached to said distal end of said hollow cable for severing the tissue sample from the organ;

a leaf spring extending between said opposing cups, said leaf being pivotally attached to each cup;

means for deflecting said leaf spring to a configuration that is concave within the proximal ends of the cups configuration for retrieving the tissue sample, and to a convex configuration for ejecting the tissue sample.

10. The biopsy forceps of claim 9, wherein said means for deflecting said leaf spring is operable from said proximal end of said cable.

11. The biopsy forceps of claim 9, further comprising a wire slidably disposed within said hollow cable, wherein said means for deflecting said leaf spring extends from a distal end of said wire.

12. The biopsy forceps of claim 9, further comprising a wire slidably disposed within said hollow cable, an operating pin operably connected to said opposing cups, and an actuator formed on a distal end of said wire, said activator having means for releasably engaging said operating pin; wherein said means for deflecting said leaf spring extends from a distal end of said actuator.

13. The biopsy forceps of claim 12, further comprising a mechanism for operably connecting said operating pin to said opposing cups, said mechanism being separated into two sides and having a central passage for said actuator.

14. In a biopsy forceps having a flexible cable with proximal and distal ends, a plurality of opposing cups on the distal end of the cable for severing and retrieving a tissue sample, a wire slidably disposed within the cable and operably attached to the opposing cups, and means for sliding the wire mounted on the proximal end of the cable; the improvement comprising resilient elongate ejection means extending between said cups for ejecting the tissue sample from the opposing cups, said ejection means operably attached to the wire.

15. The biopsy forceps of claim 14, wherein said ejection means comprises a resilient ejection band disposed between the cups and biased in a concave outward direction.

16. The biopsy forceps of claim 15, wherein the ends of the resilient ejection band are attached to the cups.

17. The biopsy forceps of claim 14, wherein said ejection means comprises a resilient ejection band disposed between the cups and an actuator formed on a distal end of the wire for releasably engaging a cup opening means, said actuator having a spring latch on a distal end for engaging said ejection band.

18. The biopsy forceps of claim 14, further comprising a means on said proximal end of said cable for sliding said wire within said cable; said sliding means including a latch for selectively preventing movement between a first position for opening the cups to retrieve a tissue sample and a second position for ejecting the tissue sample.

* * * * *

UNITED STATES PATENT AND TRADEMARK OFFICE
CERTIFICATE OF CORRECTION

PATENT NO. : 5,575,806

DATED : November 19, 1996

INVENTOR(S) : Naomi Nakao

It is certified that error appears in the above-identified patent and that said Letters Patent is hereby corrected as shown below:

Column 7,
Claim 12, line 13, delete "activator" and insert --actuator--.

Signed and Sealed this

Eleventh Day of February, 1997

*Attest:*

BRUCE LEHMAN

*Attesting Officer*  *Commissioner of Patents and Trademarks*